(12) United States Patent
Wang et al.

(10) Patent No.: US 11,077,258 B2
(45) Date of Patent: Aug. 3, 2021

(54) SUB-ASSEMBLY FOR A MEDICAMENT DELIVERY DEVICE

(71) Applicant: SHL MEDICAL AG, Zug (CH)

(72) Inventors: Hsuan Wang, Taoyuan (TW); Jung-Chien Chou, Changhua (TW); Wen-Yen Lee, Taoyuan (TW)

(73) Assignee: SHL MEDICAL AG, Zug (CH)

(*) Notice: Subject to any disclaimer, the term of this patent is extended or adjusted under 35 U.S.C. 154(b) by 277 days.

(21) Appl. No.: 16/337,681

(22) PCT Filed: Sep. 25, 2017

(86) PCT No.: PCT/EP2017/074258
§ 371 (c)(1),
(2) Date: Mar. 28, 2019

(87) PCT Pub. No.: WO2018/069032
PCT Pub. Date: Apr. 19, 2018

(65) Prior Publication Data
US 2020/0030547 A1 Jan. 30, 2020

(30) Foreign Application Priority Data
Oct. 13, 2016 (EP) .................................... 16193817

(51) Int. Cl.
A61M 5/32 (2006.01)
(52) U.S. Cl.
CPC ........ A61M 5/3213 (2013.01); A61M 5/3204 (2013.01); A61M 2005/3215 (2013.01); A61M 2207/10 (2013.01)
(58) Field of Classification Search
CPC .............. A61M 5/3204; A61M 5/3202; A61M 5/3243; A61M 5/3213; A61M 5/3257;
(Continued)

(56) References Cited

U.S. PATENT DOCUMENTS

| 7,771,397 | B1 | 8/2010 | Olson | |
|---|---|---|---|---|
| 2009/0182284 | A1* | 7/2009 | Morgan | .............. A61M 5/3202 604/198 |
| 2018/0228984 | A1* | 8/2018 | Sall | ..................... A61M 5/3204 |

FOREIGN PATENT DOCUMENTS

| CN | 101489610 A | 7/2009 |
|---|---|---|
| CN | 103764207 A | 4/2014 |

(Continued)

OTHER PUBLICATIONS

International Search Report and Written Opinion for Int. App. No. PCT/EP2017/074258, dated Dec. 15, 2017.

Primary Examiner — Manuel A Mendez
Assistant Examiner — Justin L Zamory
(74) Attorney, Agent, or Firm — McDonnell Boehnen Hulbert & Berghoff LLP

(57) ABSTRACT

The present disclosure relates to a cap assembly for a medicament delivery device, having a cap containing a tubular body provided with a distal opening, the cap being configured to be mounted to a proximal end of a medicament delivery device, a tubular remover configured to be received in the distal opening of the cap, the remover having flexible radially inwards extending grippers configured to engage with a delivery member shield, and a tubular remover insert configured to be received by the remover and configured to be fixedly attached to the cap to prevent axial displacement of the remover insert relative to the cap, wherein the remover is axially displaceable relative to the cap and relative to the remover insert, from a first position in which the grippers are pressed radially outwards by an outer surface of the remover insert, to a second position located distally relative to the first position, in which second position the grippers are arranged distally beyond the outer surface of the remover insert, enabling the grippers to flex radially (Continued)

inwards to allow engagement with a delivery member shield.

16 Claims, 6 Drawing Sheets

(58) Field of Classification Search
CPC ........ A61M 5/3219; A61M 2005/3217; A61M 2005/3215; A61M 2005/312
See application file for complete search history.

(56) References Cited

FOREIGN PATENT DOCUMENTS

| | | | |
|---|---|---|---|
| CN | 103974734 | A | 8/2014 |
| CN | 105050641 | A | 11/2015 |
| CN | 105163782 | A | 12/2015 |
| EP | 2923716 | A1 | 9/2015 |
| TW | 201509474 | A | 3/2015 |
| TW | 201544132 | A | 12/2015 |
| TW | 201603853 | A | 2/2016 |
| TW | 201625323 | A | 7/2016 |
| WO | 2014/154498 | A1 | 10/2014 |
| WO | 2015/110532 | A1 | 7/2015 |
| WO | 2016/055334 | A1 | 4/2016 |

\* cited by examiner

SUB-ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/074258 filed Sep. 25, 2017, which claims priority to European Patent Application No. 16193817.0 filed Oct. 13, 2016. The entire disclosure contents of these applications are herewith incorporated by reference into the present application.

TECHNICAL FIELD

The present disclosure generally relates to medical devices. In particular, it relates to a cap assembly for a medicament delivery device, to a sub-assembly comprising such a cap assembly, to a medicament delivery device comprising a sub-assembly, and to a method of assembling a medicament delivery device.

BACKGROUND

Medicament delivery devices, such as injectors and inhalers, typically comprise a housing in which a medicament container containing a medicament is to be arranged. Upon activation of the medicament delivery device, the medicament is expelled through a medicament delivery member, for example a needle or a nozzle.

In order to protect and to keep the medicament delivery member sterile, the medicament delivery member may be provided with a delivery member shield, or sheath, such as a Flexible Needle Shield (FNS) or a Rigid Needle Shield (RNS). The delivery member shield may thus be attached to the medicament container to cover the delivery member.

Moreover, the medicament delivery device may comprise a removable cap which is mounted to the proximal end of the housing, i.e. that end which is placed towards the injection site during medicament delivery, of the medicament delivery device, or to the proximal end of the medicament container. The removable cap has the function of providing mechanical protection of the medicament delivery member while attached to the housing or medicament container, and to remove the delivery member shield when the cap is removed from the housing.

An example of a device for removing a needle shield from an auto-injector is disclosed in WO2015110532 A1. WO2015110532 A1 discloses an auto-injector having a connector for connecting a needle cover to a removable cap. The connector has a plurality of legs spaced symmetrically away from one another about a central hub. The legs have an elastic nature and aid in securing the needle cover and/or rigid needle shield to a cap insert and hence to the removable cap. The needle cover and/or needle shield are secured together through upper, internally facing barbs protruding from the first legs. The upper, internally facing barbs include tips that point toward the forward end of the connector. These barbs are shaped to engage the needle cover and/or rigid needle shield when the needle cover and/or rigid needle shield is fitted within the connector. The barb tips apply opposing force with respect to one another when they engage the needle cover and/or rigid needle shield when the needle cover and/or rigid needle shield is fitted within the connector.

SUMMARY

According to the design disclosed in WO2015110532 A1, the legs of the connector are flexed towards each other as soon as the connector is placed in the cap insert. This bending of the legs renders it more difficult to insert the needle cover/rigid needle shield into the connector, thereby making assembly more difficult. Moreover, there is a risk that the needle sheath will make contact with the barbs during insertion. Such contact is undesirable because the forces thus exerted onto the needle shield may cause movement of the needle shield relative to the needle which it encloses, which could potentially cause coring, i.e. that the needle becomes filled with debris from the needle shield, and/or that the needle is bent.

In view of the above, a general object of the present disclosure is to provide a cap assembly for a medicament delivery device which solves or at least mitigates the problems of the prior art.

There is hence according to a first aspect of the present disclosure provided a cap assembly for a medicament delivery device, comprising: a cap having a tubular body provided with a distal opening, the cap being configured to be mounted to a proximal end of a medicament delivery device, a tubular remover configured to be received in the distal opening of the cap, the remover having flexible radially inwards extending grippers configured to engage with a delivery member shield, and a tubular remover insert configured to be received by the remover and configured to be fixedly attached to the cap to prevent axial displacement of the remover insert relative to the cap, wherein the remover is axially displaceable relative to the cap and relative to the remover insert, from a first position in which the grippers are pressed radially outwards by an outer surface of the remover insert, to a second position located distally relative to the first position, in which second position the grippers are arranged distally beyond the outer surface of the remover insert, enabling the grippers to flex radially inwards to allow engagement with a delivery member shield.

The remover insert is thus configured to flex the grippers radially outwards when the remover is in the first position. The remover is in the first position when the cap assembly is attached to a medicament delivery device. Thus, as long as the cap is mounted to a medicament delivery device, or to a body thereof, the grippers will be flexed radially outwards, allowing a delivery member shield to be inserted into the remover and the remover insert without physically contacting the grippers. Since there is generally no contact between the delivery member shield and the grippers at this stage, there is no risk of coring, and there is no risk that the delivery member becomes bent. When the cap assembly is being removed from a medicament delivery device, there will be a relative movement between the remover and the remover insert, causing the grippers to be released from their radially outwardly pressed position. The grippers will thereby be able to engage or grip a medicament delivery shield received by the tubular remover.

According to one embodiment the remover has an outer surface provided with a first radial protrusion.

The first radial protrusion is configured to engage with a delivery member cover of a medicament delivery device or sub-assembly thereof, when the cap assembly has been assembled with a medicament delivery device or a housing of a medicament delivery device. When the cap assembly is being removed from the medicament delivery device or housing, the remover will initially maintain its axial position relative to the delivery member cover due to the first radial protrusion, while the cap and the remover insert are moved in the proximal direction. The remover will thus move from the first position towards the second position, causing the grippers to flex radially inwards and engage with the delivery member shield.

According to one embodiment the first radial protrusion extends in the circumferential direction along the outer surface of the remover.

According to one embodiment the outer surface of the remover is provided with a second radial protrusion.

The second radial protrusion is configured to be arranged proximally relative to a proximal end of the delivery member cover of a medicament delivery device or a sub-assembly thereof, when the cap assembly has been assembled with a medicament delivery device or a housing of a medicament delivery device. The second radial protrusion is configured to engage with a proximal edge or rim of the delivery member cover in case the cap assembly e.g. by accident is subjected to a force that would push it further in the distal direction after it has been properly assembled with a medicament delivery device or a housing. Movement of the cap assembly is thus restricted in the distal direction.

According to one embodiment the second radial protrusion is located proximally relative to the first radial protrusion.

According to one embodiment the second radial protrusion extends in the circumferential direction along the outer surface of the remover.

According to one embodiment the remover has a proximal end portion provided with a flange.

According to one embodiment the cap has a base member defining a proximal end of the cap, and a radial surface arranged distally from the base member, which base member and radial surface delimit a remover movement space, wherein the flange of the remover is configured to be arranged in the remover movement space, thereby enabling axial movement of the flange between the base member in which the remover is in the first position and the radial surface in which the remover is in the second position.

According to one embodiment the base member is configured to be attached to the tubular body of the cap, and wherein the remover insert is configured to be fixedly attached to the base member.

There is according to a second aspect of the present disclosure provided sub-assembly for a medicament delivery device, comprising: a housing, a delivery member cover configured to be received by the housing and configured to move axially relative to the housing, and a cap assembly according to the first aspect.

According to one embodiment the cap assembly is configured to be mounted onto a proximal end of the housing, and wherein the remover is configured to be received by the delivery member cover.

According to one embodiment the first radial protrusion is configured to engage with a proximal end portion of the delivery member cover such that proximal movement of the cap causes distal movement of the remover relative to the cap, from the first position to the second position thereof.

According to one embodiment the second radial protrusion is configured to be arranged proximally from a proximal end of the delivery member cover when the cap assembly is mounted to the delivery member cover, to restrict distal movement of the remover relative to the delivery member cover.

There is according to a third aspect of the present disclosure provided a medicament delivery device comprising a sub-assembly according to the second aspect.

There is according to a third aspect provided a method of assembling a medicament delivery device, comprising: a) providing a sub-assembly comprising: a cap having a tubular body provided with a distal opening, a tubular remover received in the distal opening of the cap, the remover having flexible radially inwards extending grippers configured to engage with a delivery member shield, and a tubular remover insert received by the remover and fixedly attached to the cap to prevent axial displacement of the remover insert relative to the cap, wherein the remover is axially displaceable relative to the cap and relative to the remover insert, from a first position in which the grippers are pressed radially outwards by an outer surface of the remover insert, to a second position located distally relative to the first position, in which second position the grippers are arranged distally beyond the outer surface of the remover insert, enabling the grippers to flex radially inwards to allow engagement with a delivery member shield, a housing, and a delivery member cover having a proximal opening, b) mounting the delivery member cover inside the housing, and c) assembling the cap assembly with the delivery member cover by pushing the remover inside the delivery member cover through the proximal opening of the delivery member cover such that the remover engages with the delivery member cover.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
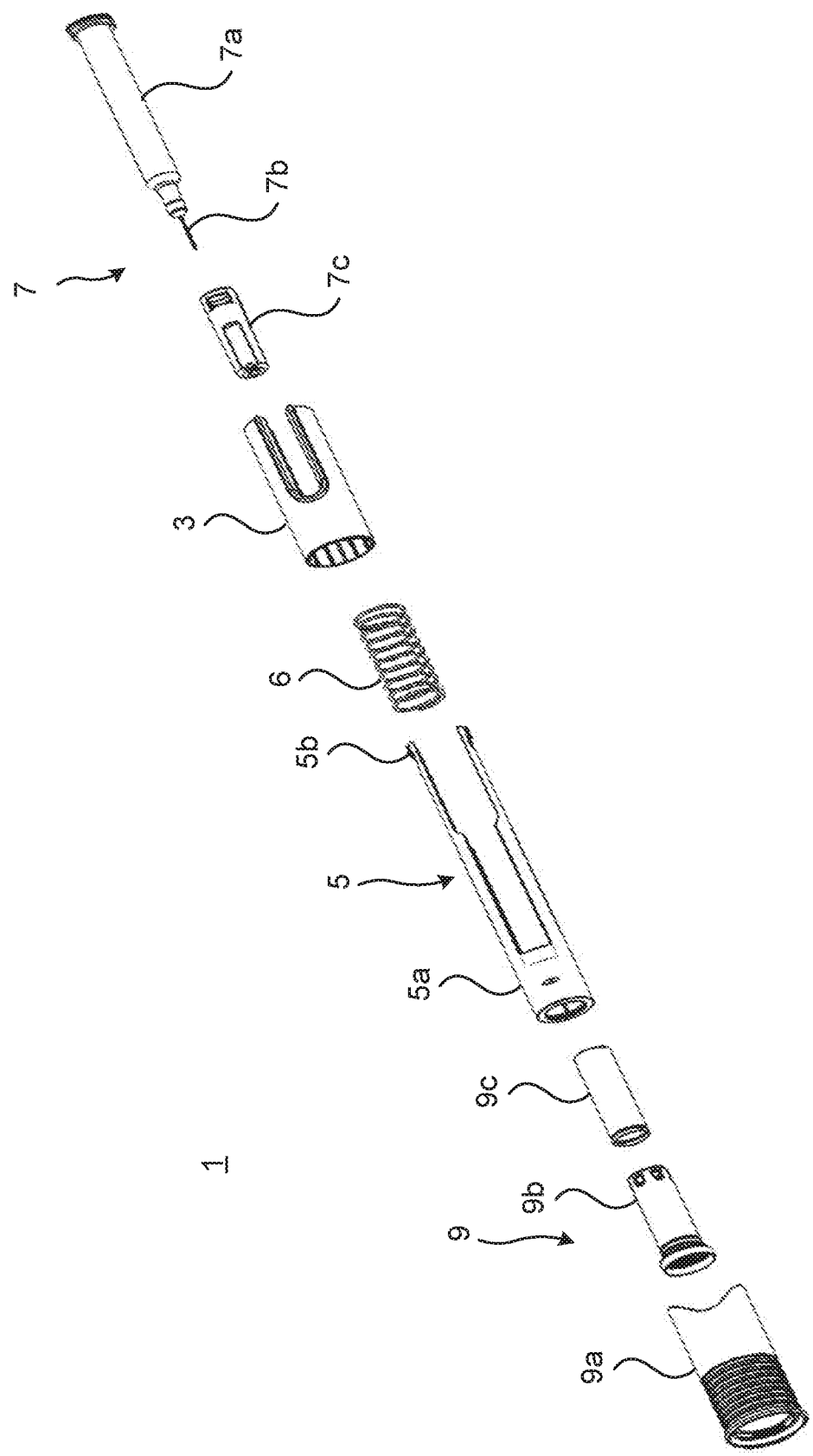
FIG. 1 is an exploded view of an example of a medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which is farthest from the proximal end of the medicament delivery device, when the cap assembly is properly mounted onto a medicament delivery device. The proximal end of a medicament delivery device is that end which is to be pointed towards the injection site during medicament injection. The same considerations also apply when referring to any component of the cap assembly. The "distal end" is the opposite end relative to the proximal end. With "proximal direction" and, equivalently, "proximally" is meant a direction from the distal end towards the proximal end, along the central axis of the safety mechanism. With "distal direction" or "distally" is meant the opposite direction to "proximal direction". The same definition also applies for the medicament container and any component thereof.

The present disclosure relates to a cap assembly for a medicament delivery device. The cap assembly includes a cap having a tubular body provided with a distal opening, a tubular remover and a tubular remover insert. The cap is configured to receive the remover through the distal opening. The remover is configured to receive the tubular remover insert. The cap, the remover and the remover insert are hence configured to be arranged in a concentric manner. The remover includes a plurality of radially flexible grippers configured to extend radially inwards to engage with a delivery member shield inserted into the remover and remover insert. The tubular remover insert is configured to press the grippers radially outwards when the remover insert is arranged in the remover. In this situation, the grippers will not engage with a delivery member shield received by the remover and the remover insert.

The remover insert is configured to be fixedly attached to the cap. Hereto, the remover insert is prevented from axial displacement relative to the cap.

The remover is configured to be displaceable axially relative to the cap and the remover insert. The remover is in particular displaceable between a first position and a second position relative to the cap and the remover insert. In the first position, the remover insert presses against the grippers, causing the grippers flex radially outwards, as described above. When the remover is displaced from the first position to the second position, the cap and the remover insert are moved axially in the proximal direction relative to the remover, causing the remover insert to move proximally relative to the grippers, proximally beyond the grippers, whereby the grippers are released from being pressed radially outwards by the remover insert. The grippers will thus flex radially inwards, towards their default position. The grippers will thereby be able to engage with a delivery member shield received by the tubular remover.

An example of a cap assembly will now be described, initially in the context of a medicament delivery device. FIG. 1 shows an example of a medicament delivery device 1. It is to be noted that some parts of the medicament delivery device 1 depicted in FIG. 1 are not shown, most notably the "power pack", which is an assembly that is to be installed at a distal end of the medicament delivery device, and which contains the drive mechanism for medicament expulsion from a medicament container of the medicament delivery device 1.

Medicament delivery device 1 comprises a housing or body 3, of which for illustrative purposes only a proximal portion is shown, a proximally biased delivery member cover 5 which has a tubular proximal portion 5a and a distal end 5b, and a resilient member 6, for example a spring, configured to bias the delivery member cover 5 proximally. The delivery member cover 5 is configured to be displaced relative to the housing 3, from an extended position relative to the housing 3, in which the delivery member cover 5 extends proximally from the housing 3, to a retracted position, in which the delivery member cover 5 has been displaced in the distal direction and further received by the housing 3.

The previously mentioned "power pack" may for example include a plunger rod, and a moveable sleeve which is configured to engage with and cooperate with the distal end 5b of the delivery member cover 5, such that linear displacement of the delivery member cover 5 in the distal direction, i.e. from the extended position to the retracted position, is translated to rotational motion of the movable sleeve, thereby releasing the plunger rod, enabling it to move in the proximal direction. Medicament expulsion may thus be initiated. The "power pack" will not be described in any further detail herein.

The exemplified medicament delivery device 1 also includes a medicament container assembly 7, which includes a medicament container 7a, a delivery member 7b, according to the present example a needle, and a delivery member shield 7c. The delivery member shield 7c may be a flexible needle shield (FNS) or a rigid needle shield (RNS). Rigid needle shields typically comprise a flexible inner member and a rigid outer member configured to receive the flexible inner member.

The medicament delivery device 1 further comprises a cap assembly 9 including a cap 9a, a tubular remover 9b, and a tubular remover insert 9c. The cap assembly 9 is configured to be mounted to e.g. the housing 3, to enclose the delivery member cover 5.

Figure 2:
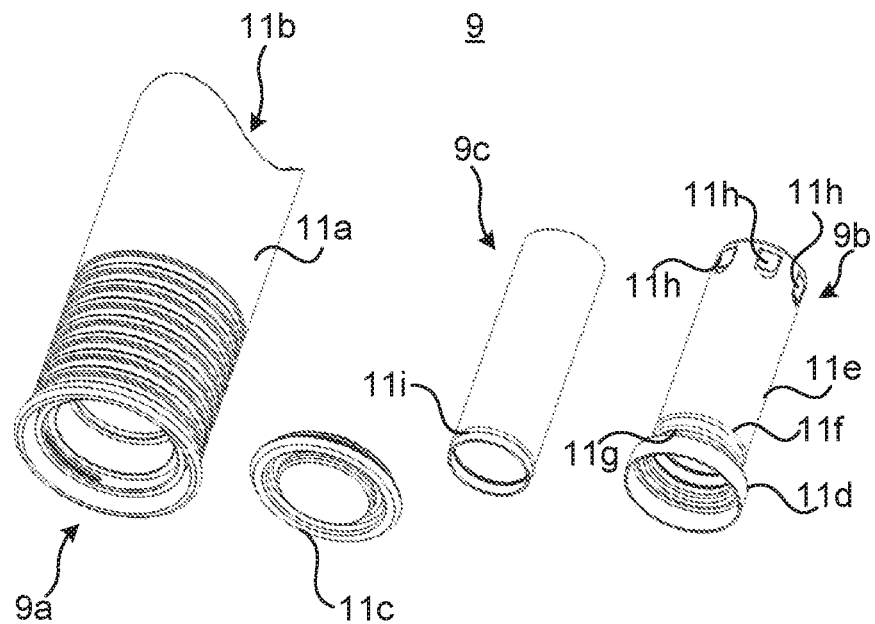
FIG. 2 is a perspective view of components of a cap assembly for the medicament delivery device in FIG. 1.

FIG. 2 shows the cap assembly 9 in more detail. The cap 9a has a tubular body 11a provided with a distal opening 11b forming a channel extending through the entire tubular body 11a. The cap 9a has a base member 11c configured to be assembled with the tubular body 11a, and defining a proximal end of the cap 9a. The proximal end opening of the cap 9a is hence closable by means of the base member 11c.

The tubular body 11a is configured to receive the remover 9b. The remover 9b is configured to receive the remover insert 9c. The remover insert 9c is configured to receive the delivery member shield 7c. The remover 9b is designed to extend beyond the remover insert 9c in the distal direction, when the remover insert 9c is arranged inside the remover 9b.

The remover 9b has a remover body which has a base that is wider than the remainder of the remover body. The base forms the proximal end portion of the remover 9b and forms a flange 11d.

The exemplified remover 9b has an outer surface 11e provided with a first radial protrusion 11f above the base or flange 11d, i.e. distally relative to the flange 11d. The first radial protrusion 11f extends circumferentially around the remover 9c, along the outer surface 11e thereof. The first radial protrusion 11f may for example be a circumferentially extending rib.

According to one variation, the outer surface 11e of the remover 9b may be provided with a second radial protrusion 11g above the base or flange 11d, i.e. distally relative to the flange 11d. The second radial protrusion 11g extends circumferentially around the remover 9b, along the outer surface 11e thereof. The second radial protrusion 11g may for example be a circumferentially extending rib. The second radial protrusion 11g may be arranged proximally relative to the first radial protrusion 11f. The second radial protrusion 11g is hence arranged axially between the first radial protrusion 11f and the flange 11d.

The remover 9c furthermore comprises a plurality of grippers 11h, for example prongs, arranged along the circumference of the remover 9b. The grippers 11h are radially flexible and extend radially inwards relative to an inner wall of the remover 9b. The grippers 11h are configured to engage with the delivery member shield 7c when the delivery member shield 7c is received by the remover 9b.

The grippers 11h are located distally from the first radial protrusion 11f. According to one variation a distal end portion of the remover 9b may be provided with the grippers 11h. The grippers 11h may have an increasing radially inwards extension in the proximal direction, as shown in FIG. 2. The distal ends of the grippers 11h may hence be attached to the remover body. Alternatively, the grippers may have an increasing radially inwards extension in the distal direction. In this case, the proximal ends of the grippers may be attached to the remover body.

The exemplified remover insert 9c has a third radial protrusion 11i configured to engage with the cap 9a. The third radial protrusion 11i may extend in the circumferential direction along the outer surface of the remover insert 9c. According to present the example, the proximal end portion of the remover insert 9c is provided with the third radial protrusion 11i.

Figure 3:
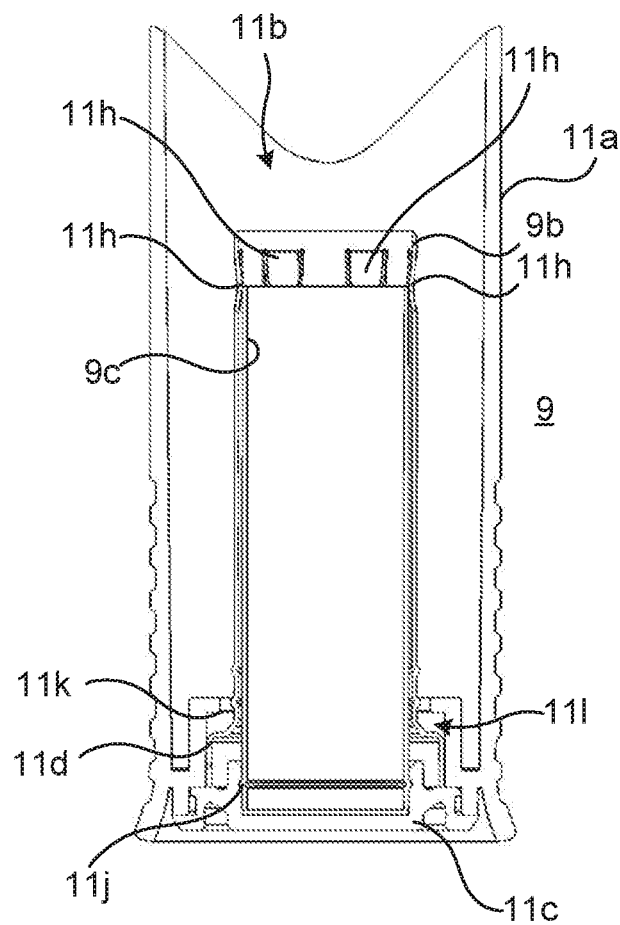
FIG. 3 shows a longitudinal section of the cap assembly in an assembled state.

According to the present example, the base member 11c has a distal opening forming a channel configured to receive the proximal end portion of the remover insert 9c. The inner walls of the base member 11c, forming the channel are provided with a circumferential groove 11j configured to receive the third radial protrusion 11i of the remover insert 9c, as shown in FIG. 3. The remover insert 9c is thus configured to engage with the cap 9a. The remover insert 9c is thereby prevented from axial movement relative to the cap 9a.

FIG. 3 shows the cap assembly 9 in an assembled state. The base member 11c has been mounted to the tubular body 11a of the cap 9a. The base member 11c may be attached to the tubular body 11a by means of engagement means such as snap-lock features, by means of glue, screws, rivets, or by means of any other suitable means for fixing two components to each other.

Figure 4:
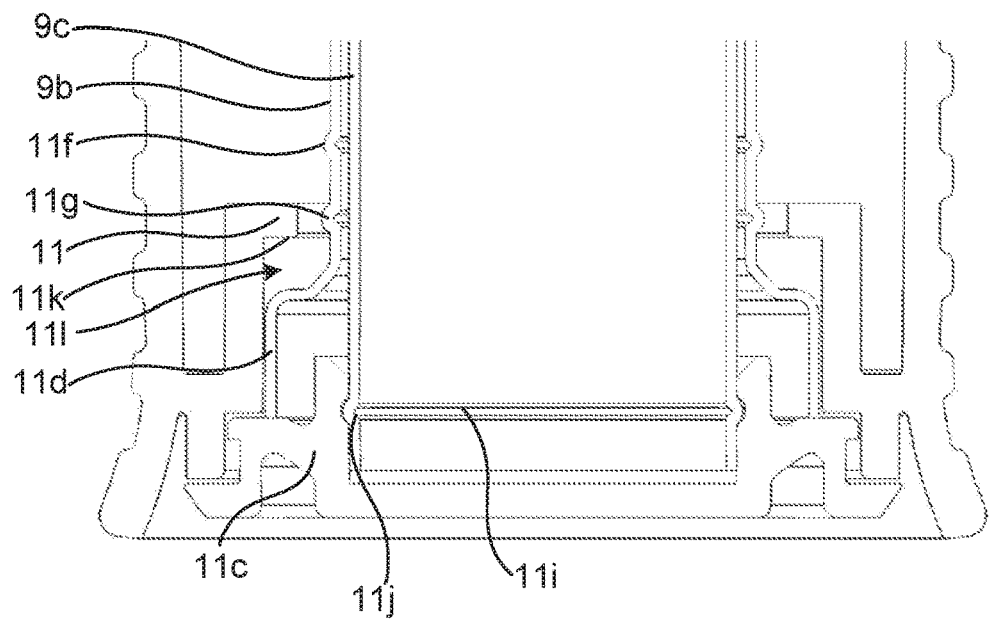
FIG. 4 is a close-up view of a proximal portion of the cap assembly shown in FIG. 3.

The cap 9a has a flange 11 extending circumferentially inside the tubular body 11a of the cap 9a. The flange has a radial surface 11k. The radial surface 11k and the base member 11c delimit a remover movement space 11l in which the base or flange 11d of the remover 9b is configured to be received, as shown in more detail in FIG. 4. The axial distance from the base member 11c and the radial surface 11k is substantially longer than the axial dimension of the base or flange 11d of the remover. A play is hence formed inside the remover movement space 11l. The flange 11d is thus able to move axially inside the remover movement space 11l. When the flange 11d contacts the base member 11c, the remover 9b is in a first position relative to the cap 9a and the remover insert 9c. When the flange 11d contacts the radial surface 11k, the remover 9b is in a second position relative to the cap 9a and the remover insert 9c.

As can be seen in FIG. 3, in an assembled state, in which the remover 9b is in the first position, the remover insert 9c extends beyond the distal ends of the grippers 11h. The outer diameter of the remover insert 9c essentially corresponds to the inner diameter of the remover 9b. There is hence generally a friction fit between the remover insert 9c and the remover 9b. The outer surface of the remover insert 9c presses the grippers 11h radially outwards from their default radially inwards extending position.

Figure 5:
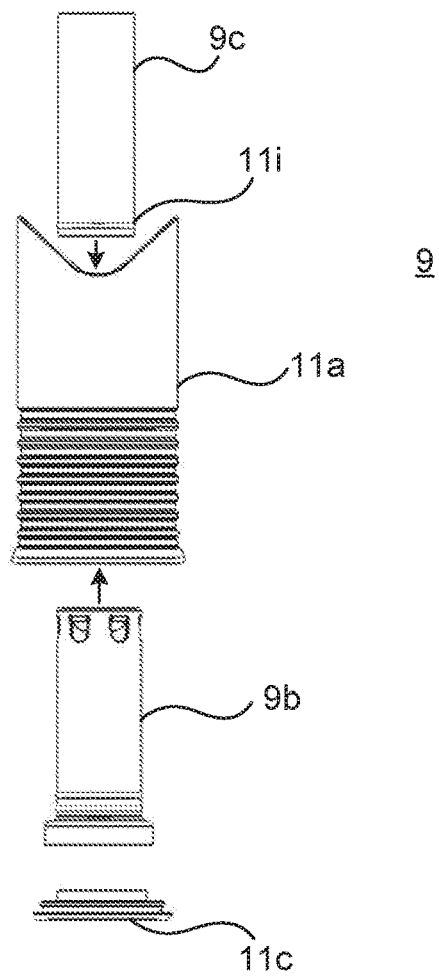
FIG. 5 is a side exploded view of the cap assembly in FIG. 2.

FIG. 5 shows schematically the procedure of assembling the cap assembly 9. Due to the existence of the flange 11d of the remover 9b, the remover 9b is placed into the tubular body 11a of the cap 9a from a bottom end, or proximal end, thereof before the base member 11c is attached to close the proximal end opening of the cap 9a. Next, the remover insert 9c is inserted into the remover 9b and into the tubular body 11a of the cap 9a, from a distal end of the cap 9a, through the distal opening 11b. When inserted into the cap 9a the remover insert 9c is attached to the cap 9a, according to the example by snapping the third radial protrusion 11i into the circumferential groove 11j of the base member 11c.

Figure 6:
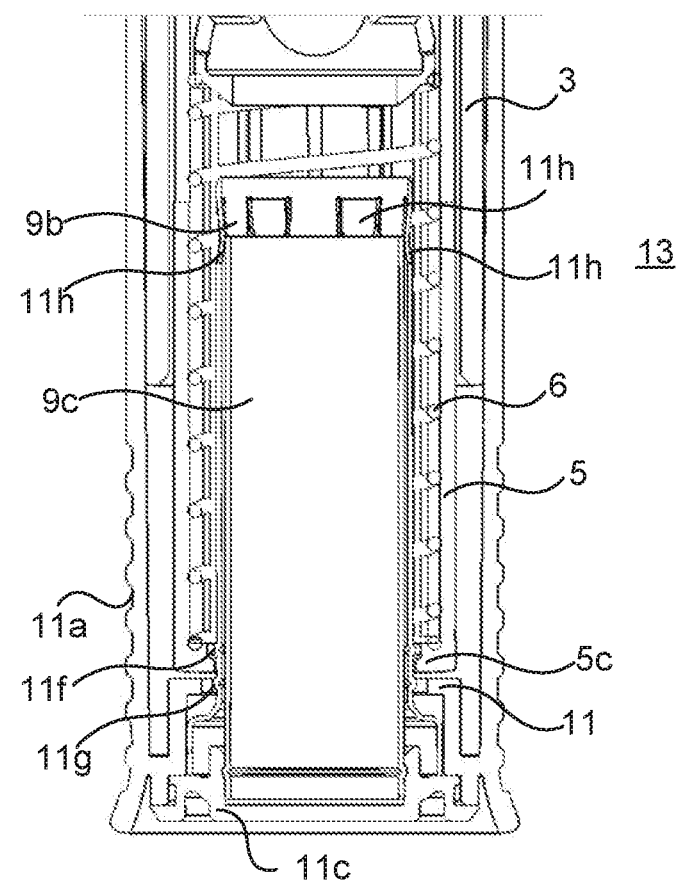
FIG. 6 is a longitudinal section of a sub-assembly including the cap assembly in FIG. 2.

FIG. 6 shows a sub-assembly 13 of the medicament delivery device 1. The sub-assembly 13 includes the cap assembly 9, the delivery member cover 5 and the housing or body 3.

The delivery member cover 5 is configured to extend into the tubular body 11a of the cap 9a. The delivery member cover 5 is configured to extend coaxially with and radially outside of the remover 9b and the remover insert 9c, but radially inwards of the outer walls of the tubular body 11a.

In the mounted state shown in FIG. 6, the proximal end of the delivery member cover 5 is located just above, i.e. distally from, the flange 11 inside the cap 9a. The first radial protrusion 11f is arranged inside the delivery member cover 5, distally from a proximal flange 5c of the delivery member cover 5. The first radial protrusion 11f will thus engage with the delivery member cover 5 when the cap assembly 9 is moved in the proximal direction, away from the housing 3, initially causing the remover 9b to maintain its axial position in which it engages with the delivery member cover 5, while the remover insert 9c slides in the proximal direction relative to the remover 9b. The function of the cap assembly 9 will be described in more detail with reference to FIGS. 8a-8c.

The second radial protrusion 11g is located outside of the delivery member cover 5, proximally from the proximal end of the delivery member cover 5.

Figure 7:
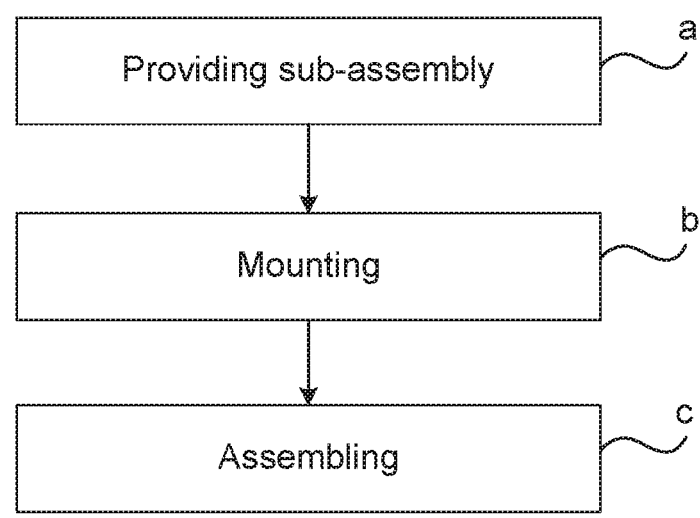
FIG. 7 is a flow chart of a method of assembling a medicament delivery device.

FIG. 7 shows a method of assembling the medicament delivery device 1, or, alternatively a method of assembling the sub-assembly 13.

In a step a) the sub-assembly 13 comprising the cap assembly 9, the housing 3 and the delivery member cover 5 is provided.

In a step b) the delivery member cover 5 is mounted inside the housing 3.

In a step c) the cap assembly 9 is assembled with the delivery member cover 5 by pushing the remover 9b inside the delivery member cover 5 through a proximal opening of the delivery member cover 5 such that the remover 9b engages with the delivery member cover 5. In particular, the first radial protrusion 11f is moved inside the delivery member cover 5 for engagement with the delivery member cover 5. The remover 9b is placed in the first position relative to the remover insert 9c by ensuring that the flange 11d of the remover 9b contacts the base member 11c.

Subsequently, the medicament container assembly 7 may be placed inside the housing 3, through a distal end of the housing 3. The delivery member 7b, and the delivery member shield 7c enclosing the delivery member 7b will thereby be received inside the remover insert 9c and thus inside the remover 9b. Since the remover 9b is in the first position relative to the remover insert 9c, the grippers 11h are pressed radially outwards by the remover insert 9c. At a later stage, the "power pack" may be mounted from a distal end of the housing 3.

Figure 8A:
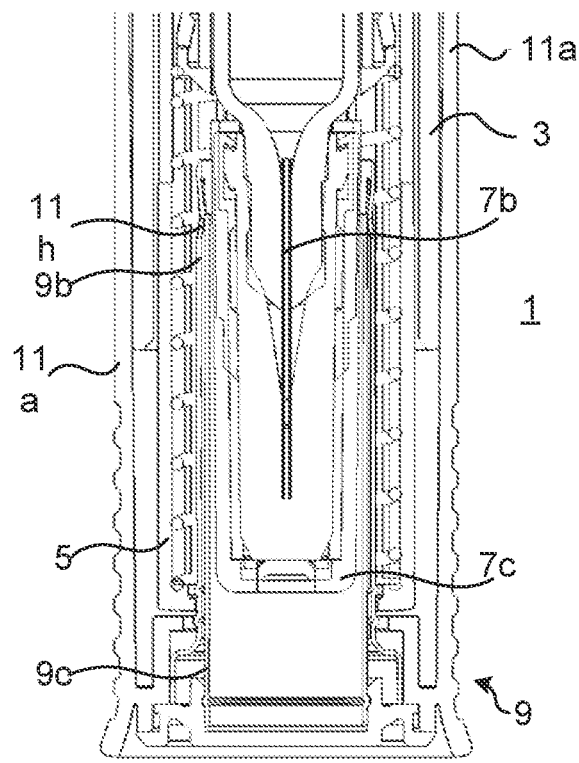
FIGS. 8a-8c show longitudinal sections of a medicament delivery device and the cap assembly in use, in particular at various stages of removal of the cap assembly from a medicament delivery device.
Figure 8B:
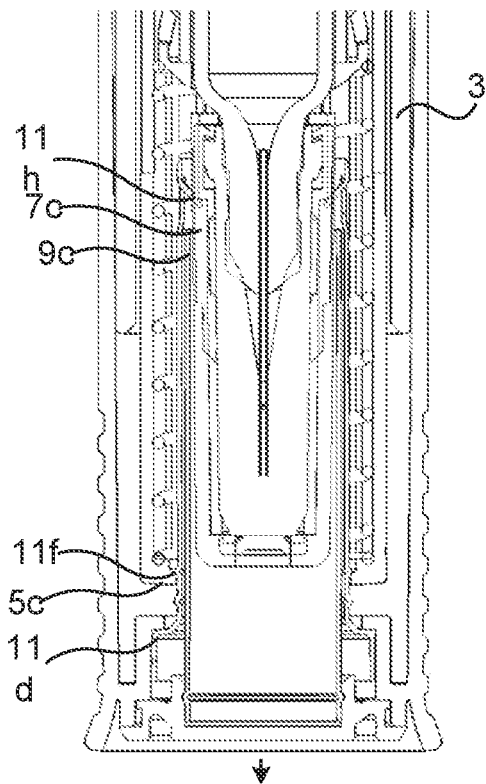
Figure 8C:
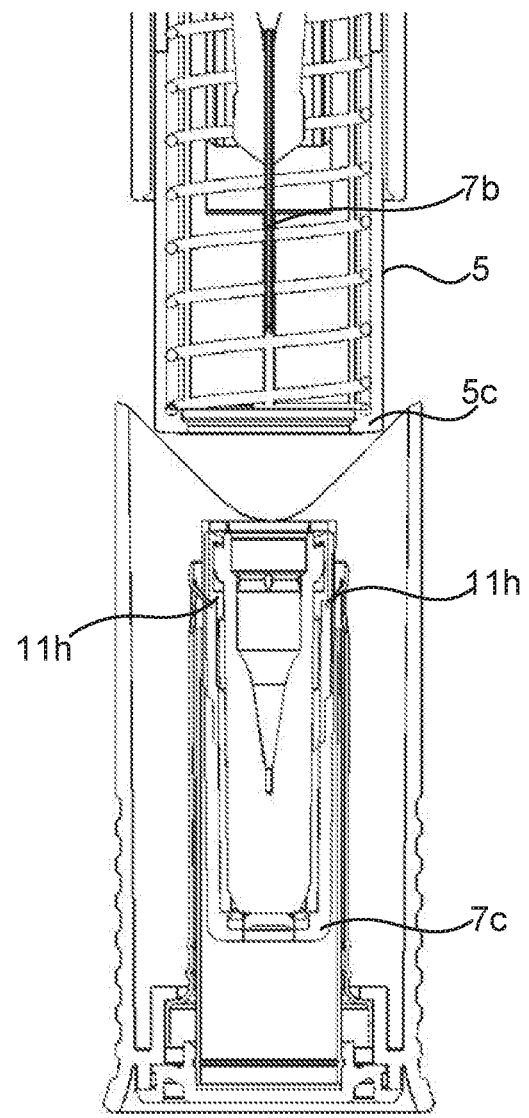

Turning now to FIGS. 8a-8c, the procedure of removing the cap assembly and the delivery member shield 7c from the medicament delivery device 1 will now be described in more detail.

In FIG. 8a, the cap assembly 9 is fully assembled with the housing 3, and the remover insert 9c presses the grippers 11h radially outwards. The remover 9b is in the first position relative to the remover insert 9c.

In FIG. 8b, the cap assembly 9 removal has commenced and the cap assembly 9 has been moved in the proximal direction relative to the housing 3, as shown by the downwards arrow. The first radial protrusion 11f engages with the proximal flange 5c of the delivery member cover 5, causing the remover 9b to maintain a fixed axial position relative to the delivery member cover 5 while the cap 9a and the remover insert 9c are moved away from the housing 3. This relative movement between the remover 9b and the remover insert 9c is made possible by the play inside the remover movement space 11l. By this motion, the remover 9b eventually obtains the second position relative to the remover 9c and the cap 9a. The grippers 11h are thus released in this process, allowing them to flex radially inwards, towards their default position. This causes the grippers 11h to engage with a distal portion of the delivery member shield 7c.

As shown in FIG. 8c, when the cap assembly 9 is pulled further in the proximal direction, with a force greater than what the engagement between the delivery member cover 5 and the first radial protrusion 11f can withstand, the first radial protrusion 11f will eventually move past the proximal flange 5c of the delivery member cover 5 and the cap assembly 9 will be removed from the medicament delivery device 1. Since the grippers 11h engage with the delivery member shield 7c, the delivery member shield 7c is removed concurrently with the cap assembly 9 and is thus removed from the delivery member 7b. The medicament delivery device 1 will as a result be ready for medicament administration.

The disclosed concept has mainly been described above with reference to a few examples. However, as is readily appreciated by a person skilled in the art, other embodiments than the ones disclosed above are equally possible within the scope of the disclosed concept, as defined by the appended claims.

The invention claimed is:

1. A sub-assembly for a medicament delivery device, which sub-assembly comprises:
   a housing;
   a delivery member cover configured to be received by the housing and configured to move axially relative to the housing; and
   a cap assembly comprising:
   a cap having a tubular body provided with a distal opening, the cap being configured to be mounted to a proximal end of a medicament delivery device;
   a tubular remover configured to be received in the distal opening of the cap, the remover having flexible radially inwards extending grippers configured to engage with a delivery member shield; and
   a tubular remover insert configured to be received by the remover and configured to be fixedly attached to the cap to prevent axial displacement of the remover insert relative to the cap,
   wherein the remover is axially displaceable relative to the cap and relative to the remover insert from a first position in which the grippers are pressed radially outwards by an outer surface of the remover insert to a second position located distally relative to the first position, where in the second position the grippers are arranged distally beyond the outer surface of the remover insert enabling the grippers to flex radially inwards to allow engagement with a delivery member shield, and wherein the cap assembly is configured to be mounted onto a proximal end of the housing, and wherein the remover is configured to be received by the delivery member cover.

2. The sub-assembly as claimed in claim 1, wherein the remover has an outer surface provided with a first radial protrusion.

3. The sub-assembly as claimed in claim 2, wherein the first radial protrusion extends in the circumferential direction along the outer surface of the remover.

4. The sub-assembly as claimed in claim 2, wherein the outer surface of the remover is provided with a second radial protrusion.

5. The sub-assembly as claimed in claim 4, wherein the second radial protrusion is located proximally relative to the first radial protrusion.

6. The sub-assembly as claimed in claim 4, wherein the second radial protrusion extends in the circumferential direction along the outer surface of the remover.

7. The sub-assembly as claimed in claim 4, wherein the remover has a proximal end portion provided with a flange.

8. The sub-assembly as claimed in claim 7, wherein the cap has a base member defining a proximal end of the cap and a radial surface arranged distally from the base member, where the base member and radial surface delimit a remover movement space,
   wherein the flange of the remover is configured to be arranged in the remover movement space thereby enabling axial movement of the flange between the base member when the remover is in the first position and the radial surface when the remover is in the second position.

9. The sub-assembly as claimed in claim 8, wherein the base member is configured to be attached to the tubular body of the cap, and wherein the remover insert is configured to be fixedly attached to the base member.

10. The sub-assembly as claimed in claim 2, wherein the first radial protrusion is configured to engage with a proximal end portion of the delivery member cover such that proximal movement of the cap causes distal movement of the remover relative to the cap, from the first position to the second position thereof.

11. The sub-assembly as claimed in claim 4, wherein the second radial protrusion is configured to be arranged proximally from a proximal end of the delivery member cover when the cap assembly is mounted to the delivery member cover to restrict distal movement of the remover relative to the delivery member cover.

12. A medicament delivery device comprising the sub-assembly of claim 1.

13. A medicament delivery device comprising the sub-assembly of claim 9.

14. The medicament delivery device as claimed in claim 12, wherein the medicament delivery device further comprises a medicament container assembly inside the housing and a power pack.

15. A method of assembling a medicament delivery device, comprising the steps of:
   a) providing a sub-assembly comprising:
      a cap having a body provided with a distal opening;

a remover received in the distal opening of the cap, the remover having flexible radially inwards extending grippers configured to engage with a delivery member shield;

a remover insert received by the remover and fixedly attached to the cap to prevent axial displacement of the remover insert relative to the cap, wherein the remover is axially displaceable relative to the cap and relative to the remover insert from a first position in which the grippers are pressed radially outwards by an outer surface of the remover insert to a second position located distally relative to the first position, where in the second position the grippers are arranged distally beyond the outer surface of the remover insert enabling the grippers to flex radially inwards to allow engagement with a delivery member shield;

a housing; and a delivery member cover having a proximal opening, b) mounting the delivery member cover inside the housing, and c) connecting the cap assembly to the delivery member cover by pushing the remover inside the delivery member cover through the proximal opening of the delivery member cover such that the remover engages with the delivery member cover.

16. The method of assembling a medicament delivery device of claim 15 further comprising the steps of:

inserting a medicament container assembly inside the housing through a distal end of the housing; and mounting a "power pack" from a distal end of the housing.

* * * * *